United States Patent
Isobe et al.

(10) Patent No.: US 7,625,524 B2
(45) Date of Patent: Dec. 1, 2009

(54) AUTOMATIC ANALYZER

(75) Inventors: Tetsuya Isobe, Hitachinaka (JP); Katsuaki Takahashi, Hitachinaka (JP); Isao Yamazaki, Ryugasaki (JP)

(73) Assignees: Hitachi High-Technologies Corporation, Tokyo (JP); Hitachi Science Systems, Ltd., Ibaraki (JP)

( * ) Notice: Subject to any disclaimer, the term of this patent is extended or adjusted under 35 U.S.C. 154(b) by 465 days.

(21) Appl. No.: 10/676,020

(22) Filed: Oct. 2, 2003

(65) Prior Publication Data

US 2004/0067165 A1    Apr. 8, 2004

(30) Foreign Application Priority Data

Oct. 4, 2002    (JP)    ............... 2002-291800

(51) Int. Cl.
  G01N 21/00    (2006.01)
  G01N 31/00    (2006.01)
  B01L 3/02    (2006.01)
(52) U.S. Cl. .................. 422/63; 422/64; 422/65; 422/66; 422/67; 422/100
(58) Field of Classification Search .............. 422/63, 422/64, 100, 81, 50
See application file for complete search history.

(56) References Cited

U.S. PATENT DOCUMENTS 4,785,677 A    11/1988    Higo
4,974,457 A    12/1990    Angst et al.
5,137,693 A *   8/1992    Mawhirt ............. 422/104
5,200,151 A *   4/1993    Long ................. 422/100
5,240,679 A    8/1993    Stettler
5,863,752 A *   1/1999    Court et al. ........... 435/34

FOREIGN PATENT DOCUMENTS

JP    11-183484    7/1999
WO    WO 89/12829    12/1989
WO    WO 94/02826    2/1994

* cited by examiner

Primary Examiner—Jill Warden
Assistant Examiner—Neil Turk
(74) Attorney, Agent, or Firm—Mattingly & Malur, P.C.

(57) ABSTRACT

A highly-reliable, inexpensive and small-sized automatic analyzer is provided which can eliminate the need of an additional space for piercing a seal of a reagent bottle and can prevent a deviation of a reagent sampling nozzle from the position of a pierced hole. A piercing tool for piercing the seal of the reagent bottle is fitted over a nozzle of a reagent sampling mechanism, and a stripper for automatically fitting and removing the piercing tool is provided. By fitting the piercing tool for piercing the seal of the reagent bottle over the nozzle of the reagent sampling mechanism, the seal of the reagent bottle can be pierced in situ on a reagent disk by using the piercing tool. An additional space so far required for the seal piercing is no longer needed and a deviation between the seal piercing position and the reagent sampling position is prevented.

6 Claims, 7 Drawing Sheets

AUTOMATIC ANALYZER

BACKGROUND OF THE INVENTION

1. Field of the Invention

The present invention relates to an automatic analyzer for use in clinical examination to perform qualitative and quantitative analysis of living body samples, such as blood and urine. More particularly, the present invention relates to an automatic analyzer for use with reagent bottles having seals attached to bottle openings, which are pierced at the start of analysis using the reagent bottles.

2. Description of the Related Art

Two types of reagent bottles are mainly used in an automatic analyzer, i.e., a capped reagent bottle which is set in the automatic analyzer by an operator at the start of analysis after removing the cap, and a reagent bottle with a seal which is made of plastic, for example, is attached to a bottle opening to prevent evaporation and deterioration of the reagent, and is ripped by an operator before the start of analysis. When using the latter type of reagent bottle, it is general that the reagent bottle is set in the automatic analyzer by the operator after ripping the seal with a dedicated cutter, a punch or the like. On the other hand, various methods are also proposed so far for automatically piercing the seal by the analyzer itself when the reagent bottle is set in the analyzer. Patent Document 1 (JP, A 11-183484) discloses a method of piercing a seal by a disposable tip which is fitted to a fore end of a reagent sampling nozzle (arm) and which has a fore end formed into a shape capable of piercing the seal.

SUMMARY OF THE INVENTION

When the operator rips the seal with the dedicated cutter, punch or the like, a position at which the seal is ripped must be adjusted such that the reagent sampling arm passes the ripped portion of the seal. If the size of the ripped portion is increased, close adjustment is not required for the position of the ripped portion, but the sealing function to prevent evaporation and deterioration of the reagent is impaired.

On the other hand, the method disclosed in JP, A 11-183484 requires no adjustment for the piercing position because the fore end of the reagent sampling arm coincides with the fore end of the disposable tip for piercing the seal. In consideration of that the disposable tip and the seal of the reagent bottle are both made of plastic, however, the plastic tip is estimated to face a difficulty in piercing the plastic seal. Also, even if the disposable tip is able to pierce the seal, a risk would arise in that the tip fore end is deformed and the accuracy in, e.g., sampling the reagent lowers. In the case of using the disposable tip made of metal to facilitate piercing of the tip through the seal, the production cost will increase.

Accordingly, it is an object of the present invention to provide an automatic analyzer including a seal-piercing and reagent-sampling mechanism which is able to positively pierce a seal of a reagent bottle and to eliminate the need of adjustment for alignment between a seal piercing position and a reagent sampling position.

To achieve the above object, the present invention is constituted as follows.

In an automatic analyzer comprising a reagent bottle containing a liquid reagent and having an opening through which the reagent is sampled out of the reagent bottle, the opening being closed by a seal to shield off the reagent from an external atmosphere; a reagent sampling arm for sampling the liquid reagent in the reagent bottle to the outside through the opening; a reaction cell in which a sample is mixed with the reagent sampled by the reagent sampling arm; and measuring means for measuring reaction between the sample and the reagent, the automatic analyzer further comprises a seal piercing tool capable of being fitted over a nozzle of the reagent sampling arm to pierce the seal of the reagent bottle; a stationary container for accommodating the seal piercing tool when not used; and a mechanism for taking the seal piercing tool out of the container and fitting the seal piercing tool to the reagent sampling arm before the start of piercing the seal of the reagent bottle, and for returning the seal piercing tool to the container after the end of the seal piercing.

One or more reagent bottles each having one or more openings may be disposed, and the automatic analyzer may further comprise a reagent-sampling-arm moving mechanism for moving the reagent sampling arm on a straight line along which the openings of the one or more reagent bottles, the container, and a reagent dispensing position to the reaction cell are arranged.

The seal can be made of any suitable material so long as the material is able to positively shield off the reagent from the external atmosphere. Generally, the seal is made of, for example, paper, plastic, or a metal foil. The above expression "One or more reagent bottles each having one or more openings" is used in consideration of the following. One reagent bottle containing the same reagent may have a plurality of openings. In general, however, a plurality of reagent bottles are molded integrally with each other, and the individual reagent bottles have respective openings. Because the seal piercing tool is repeatedly used, at least a portion of the seal piercing tool brought into contact against the seal is preferably formed of a hard material, such as a metal or ceramic, so that the seal piercing ability will not reduce even after the repeated uses. Also, the contact portion of the seal piercing tool against the seal is preferably formed into a pointed shape suitable for piercing the seal.

DESCRIPTION OF THE PREFERRED EMBODIMENTS

An embodiment of the present invention will be described below with reference to FIGS. 1 to 5.

Figure 1:
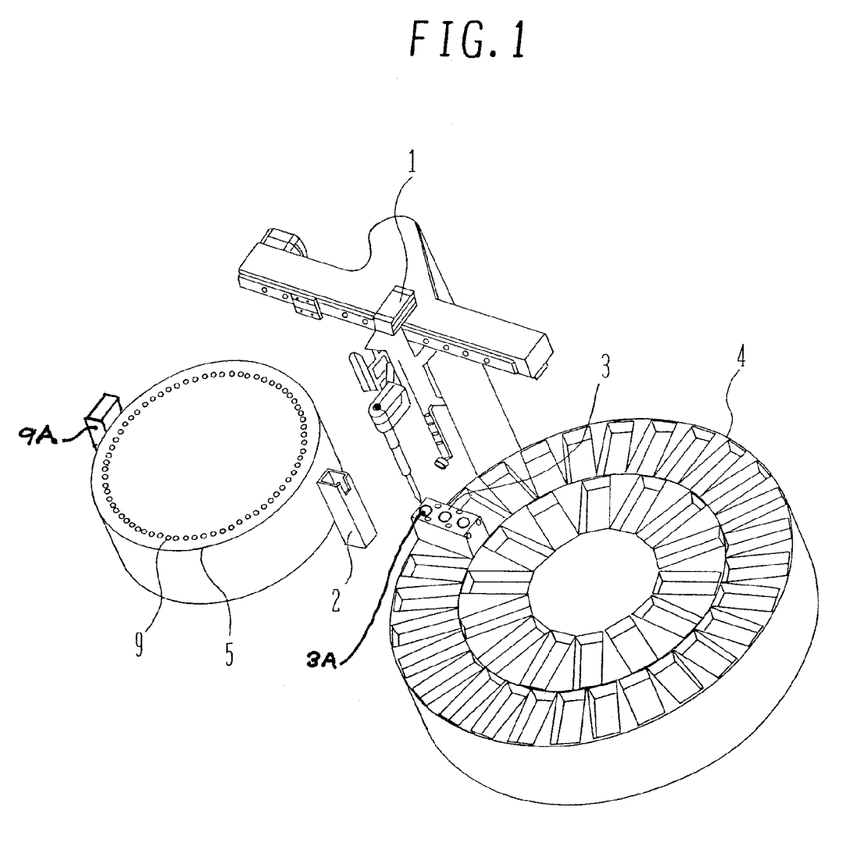
FIG. 1 schematically shows the arrangement of a mechanism system of a biochemical automatic analyzer with the reagent bottle piercing function according to the present invention.
Figure 2:
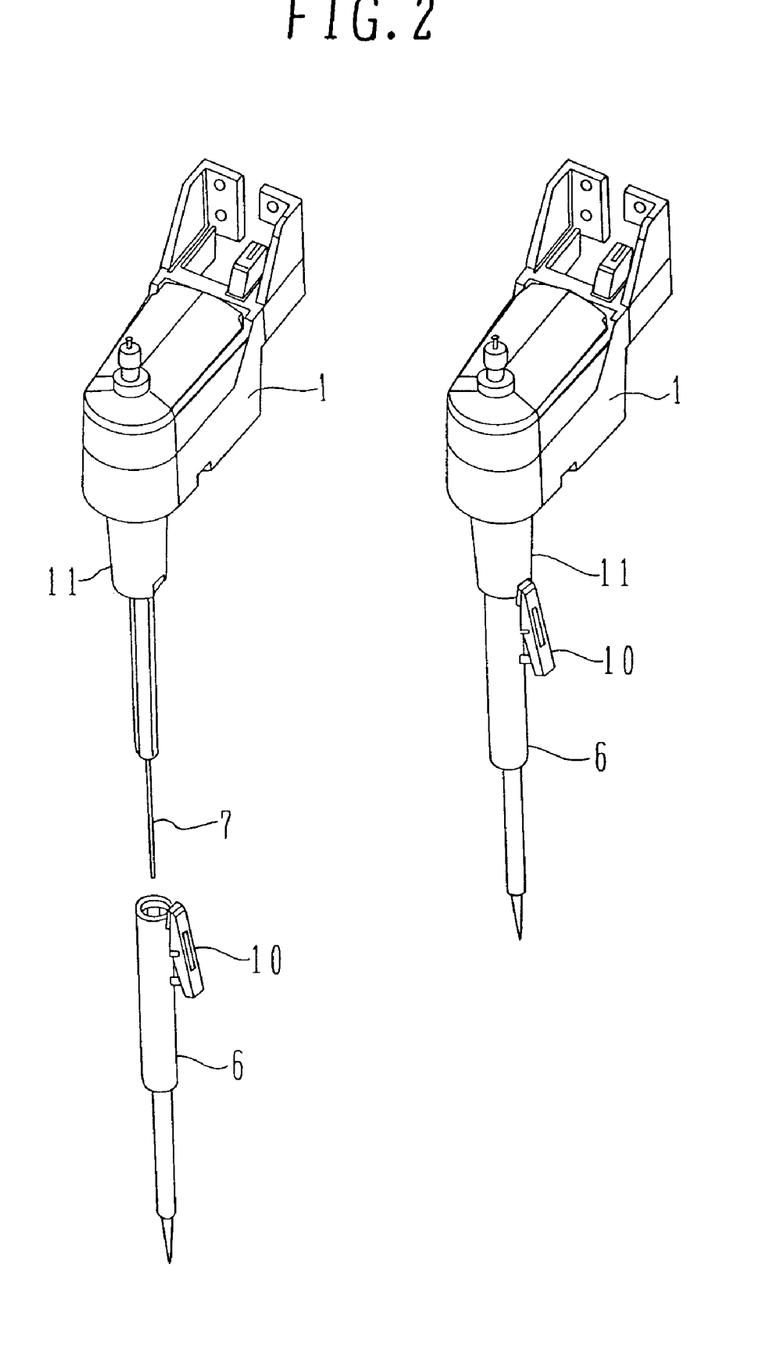
FIG. 2 shows part arrangements of a reagent sampling mechanism of the analyzer shown in FIG. 1.
Figure 3:
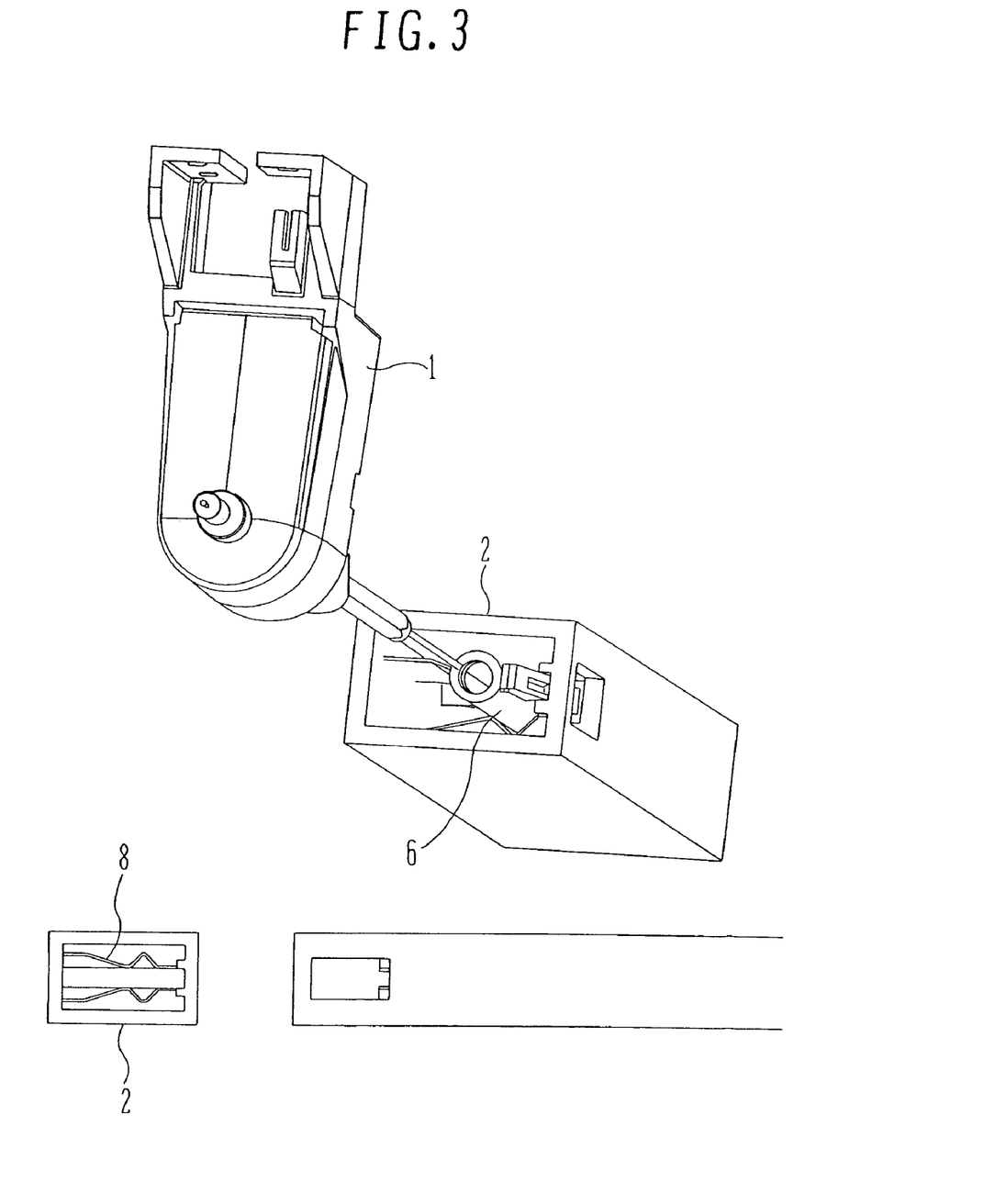
FIG. 3 shows relative positions and part arrangements of a piercing tool and a stripper of the analyzer shown in FIG. 1.

FIGS. 1 to 3 schematically show the construction of a reagent sampling mechanism 1, a reagent bottle 3, and a stripper or container 2. Those components are arranged so as to lie on a straight line. The reagent sampling mechanism 1 sucks a reagent from the reagent bottle 3 having a plurality of openings 3A placed on a reagent disk 4, carries the sucked reagent to the position of a reaction disk 5, and then delivers the reagent into a reaction cell 9 which contains a sample to be measured.

Figure 4:
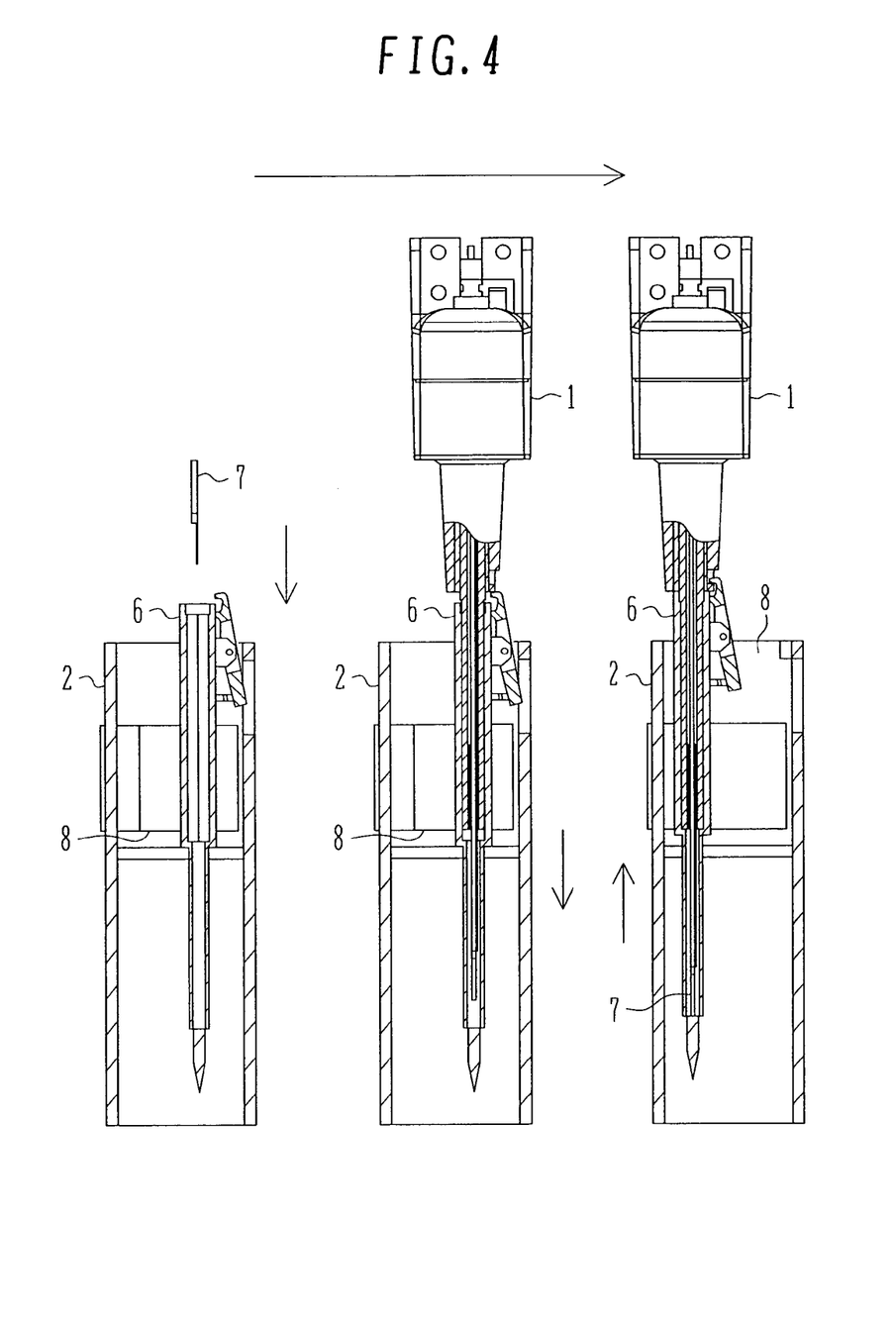
FIG. 4 is an explanatory view for explaining the operation of fitting the piercing tool of the analyzer shown in FIG. 1.
Figure 5:
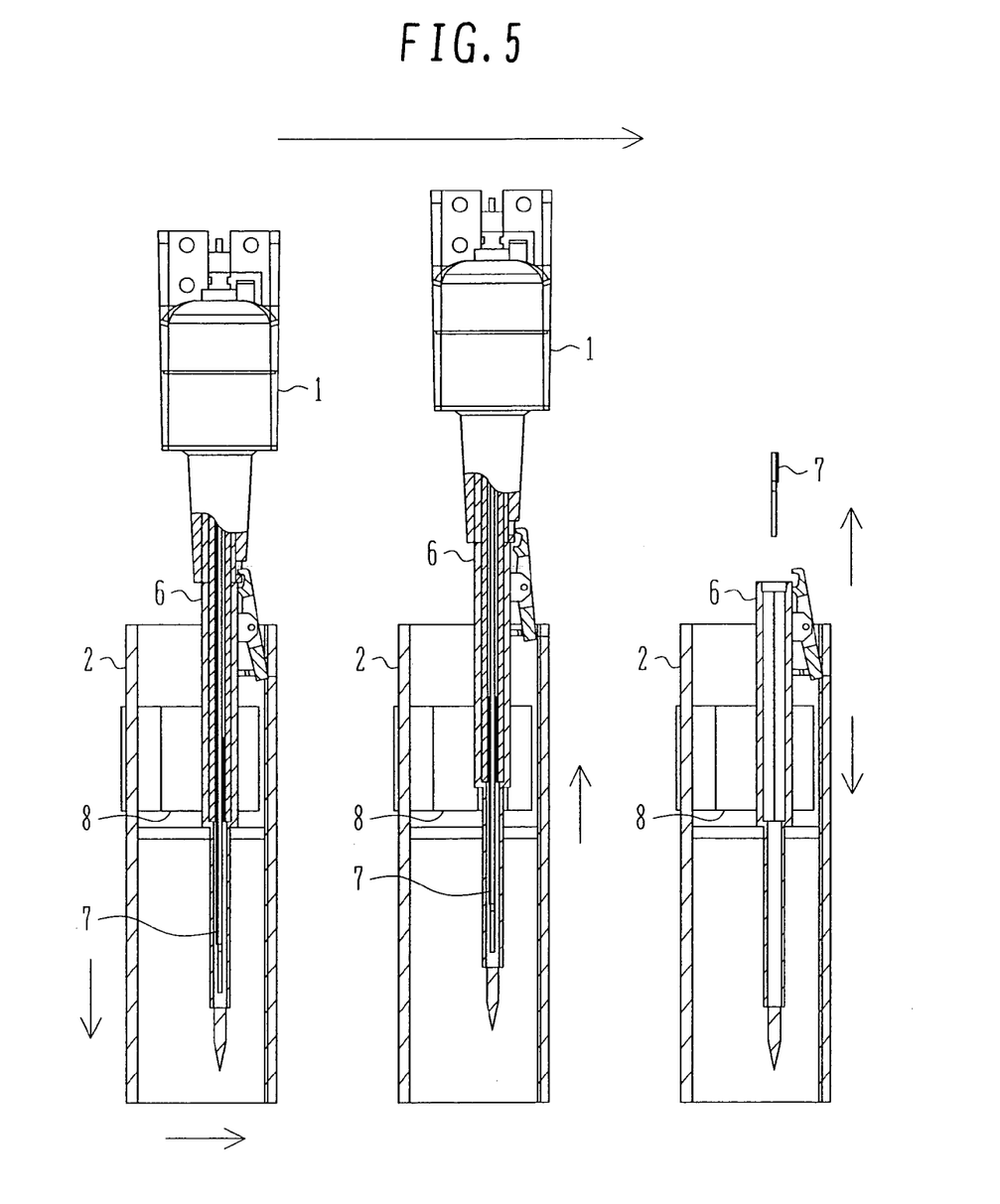
FIG. 5 is an explanatory view for explaining the operation of removing the piercing tool of the analyzer shown in FIG. 1.

FIG. 4 shows a cycle of successive steps for fitting a piercing tool 6, and FIG. 5 shows a cycle of successive steps for removing the piercing tool 6. The piercing tool 6 is used in the stage before starting analysis, i.e., at the time when an operator sets the reagent bottle 3 on the reagent disk 4. Usually, the piercing tool 6 is accommodated in the stripper 2 and is fixedly positioned by two leaf springs 8 (see also FIG. 3). Prior to starting the analysis, the operator places a plurality of reagent bottles 3 one by one on the reagent disk 4 in order through a predetermined loading inlet. The reagent bottles 3 are each provided with identification information and are registered in the analyzer by reading the identification information before the reagent bottles 3 are placed on the reagent disk 4. Upon completion of the placement of the reagent bottles 3, the reagent sampling mechanism 1 is moved from a standby position to the position of the stripper 2. Then, as shown in FIG. 4, the piercing tool 6 is attached to a nozzle 7. The piercing tool 6 has a hollow inner space into which the nozzle 7 is inserted. When the nozzle 7 is inserted into the piercing tool 6, a body 11 of the nozzle 7 contacts with a lever 10 provided on the piercing tool 6 (see also FIG. 2). A portion of the body 11 contacting with the lever 10 is formed to have a tapered surface so that the lever 10 is opened along the tapered surface. The body 11 has a slot formed therein to catch the lever 10, and the lever 10 is locked in the slot of the body 11 by a spring force. The piercing tool 6 is thereby fitted over the nozzle 7.

Subsequently, the reagent sampling mechanism 1 including the piercing tool 6 fitted over the nozzle 7 is moved to a sampling position on the reagent disk 4. Then, the reagent sampling mechanism 1 is vertically moved to pierce the seals of the reagent bottles 3 one by one. Upon completion of the seal piercing of one reagent bottle 3, the reagent disk 4 is rotated and the reagent sampling mechanism 1 starts the operation of piercing the seal of the next reagent bottle.

When the seal piercing operation is completed for all of the reagent bottles 3, the reagent sampling mechanism 1 is moved to the position of the stripper 2 where the piercing tool 6 is removed as shown in FIG. 5. The stripper 2 has a hole formed in its wall to allow insertion of a part of the lever 10. Accordingly, with only lateral movement of the reagent sampling mechanism 1, the lever 10 of the piercing tool 6 is not unlocked from the body 11 of the nozzle 9. When the reagent sampling mechanism 1 is moved upward, a lower part of the lever 10 contacts with an upper edge of the hole in the stripper wall, whereby the lever 10 starts to open. Upon full opening of the lever 10, the lever 10 is unlocked from the nozzle body 11 and the piercing tool 6 is removed from the nozzle body 11. The removed piercing tool 6 is moved downward while being guided by the leaf springs 8, and is returned to the original set position. The stripper 2 has a lever guide to prevent the piercing tool 6 from deviating from the original set position when it returns to there.

The reagent sampling mechanism 1, from which the piercing tool 6 has been removed, is moved to the standby position and stands ready for the next operation.

Figure 6A:
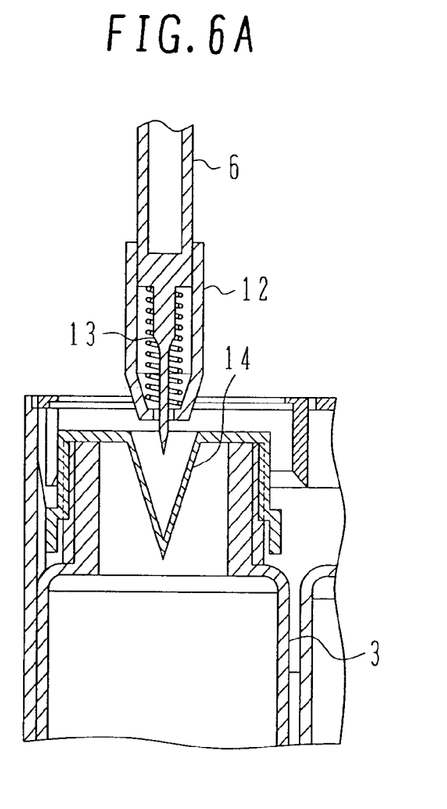
FIGS. 6A and 6B show the piercing tool additionally provided with a guide tube fitted over the tool to be slidable along an outer surface.
Figure 6B:
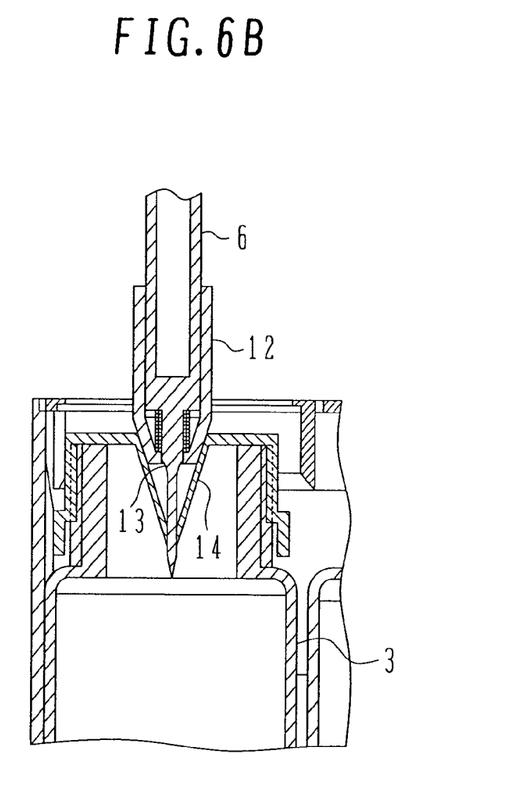
Figure 7:
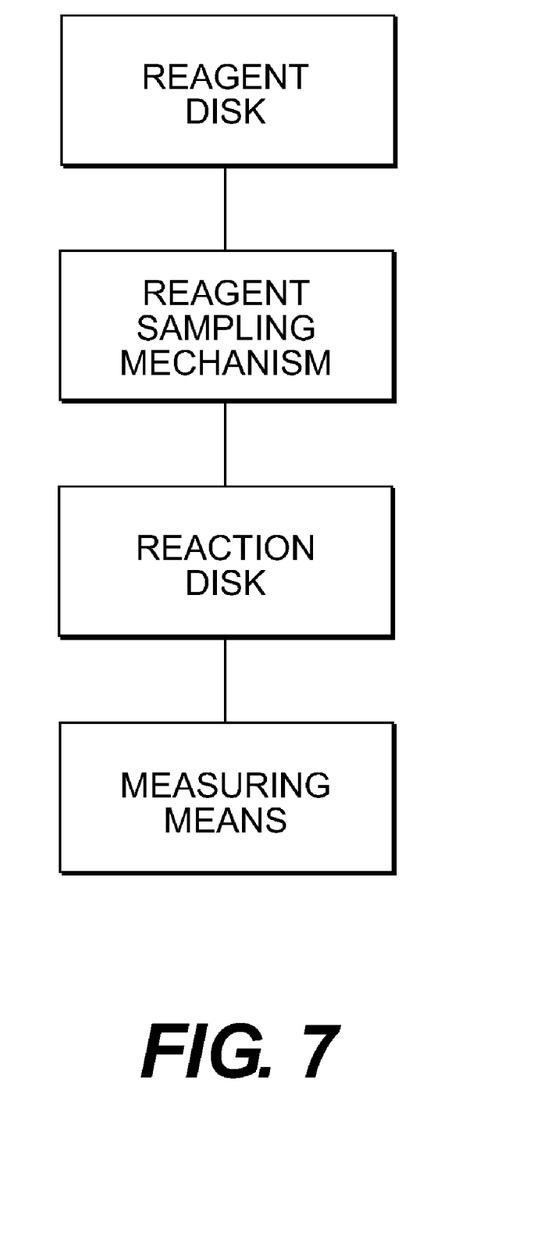
FIG. 7 is a block diagram illustrating the structural elements of the analyzer shown in FIG. 1.

FIGS. 6A and 6B show another embodiment. In this embodiment, a slidable guide tube 12 is additionally fitted over the piercing tool 6. The guide tube 12 is biased downward by a spring 13 and hence held in a cushioned state. On the reagent bottle side, a plastic seal having a tapered recess 14 is attached to a bottle opening.

FIG. 6A shows a state during downward movement of the piercing tool 6. FIG. 6B shows a state in which the piercing tool 6 is further moved downward and the guide tube 12 is engaged in the tapered recess 14. In the state of FIG. 6B, the guide tube 12 is stopped and the piercing tool 6 is pressed downward through a spring cushion, i.e., with compression of the spring 13. Thus, the piercing operation is completed by a pointed needle of the piercing tool 6. When such a reagent bottle with the seal having the tapered recess 14 is used, it is very important to accurately position both the pointed needle and the reagent bottle relative to each other. With no provision of the guide tube 12, the pointed needle pierces into the tapered surface of the recess 14 instead of the center of the tapered recess 14, i.e., a central lowermost portion thereof, if there is a deviation between the pointed needle and the reagent bottle. In the event of a hole being thus formed in the tapered surface of the recess 14, the following trouble occurs. When the sampling nozzle 7 is even slightly deviated from the center of the tapered recess 14 in the step of sampling the reagent, the nozzle is moved downward while sliding over the tapered surface and then strikes against the central lowermost portion of the tapered recess 14 (now not holed), whereby the nozzle is bent. In this embodiment, with the provision of the guide tube 12 as shown in FIG. 6, the pointed needle and the reagent bottle can be accurately positioned relative to each other in spite of a slight deviation between them. As a result, a hole can be always formed at the center of the tapered recess 14.

According to the present invention, in the automatic analyzer using the reagent bottle with the seal, the piercing tool 6 for piercing the seal of the reagent bottle 3 is fitted over the reagent sampling nozzle 7 of the reagent sampling mechanism 1, and the operation of piercing the seal of the reagent bottle can be performed on the reagent disk 4. A highly-reliable, inexpensive and small-sized automatic analyzer can be hence provided which no longer needs an additional space that has been so far required for the seal piercing and can prevent a deviation between the position of a pierced hole and the position of the nozzle 7.

What is claimed is:

1. An automatic analyzer for use with at least one reagent bottle having at least one opening for extracting a reagent contained therein, said opening being closed by a puncturable seal member for sealing a reagent from outside atmosphere, said analyzer comprising:

a reagent extracting and dispensing mechanism having a reagent probe with a nozzle for extracting and dispensing a reagent in said reagent bottle through said opening of said reagent bottle;

a reaction cell in which a sample to be analyzed is mixed with said reagent extracted and dispensed from said reagent bottle;

measuring means for measuring a reaction between said sample and said reagent extracted and dispensed from said reagent bottle;

a piercing tool to be attached to said nozzle for piercing the puncturable seal member, said piercing tool being removable from said nozzle, said piercing tool having a hollow interior into which said nozzle is inserted from one end of said piercing tool, an opposite end of said piercing tool being a pointed needle having no opening therein, and a container for holding said piercing tool before said piercing tool is attached to said nozzle, and for holding said piercing tool after said piercing tool is removed from said nozzle, a mechanism for taking said piercing tool out of said container and fitting said piercing tool to said nozzle before the start of piercing the puncturable seal of said at least one reagent bottle, and for returning said piercing tool to said container after the end of the piercing of the puncturable seal, wherein said piercing tool comprises a lever locking said piercing tool to said nozzle when said nozzle is inserted therein to prevent said piercing tool from slipping off from said nozzle, and wherein said container has means for unlocking said lever from said nozzle to remove said piercing tool from said nozzle.

2. An automatic analyzer according to claim 1, further comprising a reagent sampling mechanism for moving said nozzle downwardly to insert said nozzle into said piercing tool to be locked therein with said lever, for moving said nozzle upwardly to remove said nozzle with said piercing tool locked thereto from said container, for inserting said nozzle with said piercing tool locked thereto back into said container and for moving said nozzle upwardly to move said lever, to unlock said lever from said nozzle.

3. An automatic analyzer according to claim 1, further comprising;

a rotatable reagent disk on which a plurality of reagent bottles are arranged along a circumference of said disk; and a reagent sampling mechanism for moving said nozzle with said piercing tool locked thereto to a reagent dispensing position of said reagent disk, and moving said nozzle with said piercing tool locked thereto downwardly to pierce a seal of each said reagent bottles, respectively when each said reagent bottle is moved underneath said piercing tool by rotating said reagent disk.

4. An automatic analyzer according to claim 1, further comprising;

a reagent sampling mechanism for moving said nozzle, wherein said at least one reagent bottle has a plurality of openings, with each of said openings closed by a puncturable seal and said openings, said container, and a reagent dispensing position to dispense a reagent into said reaction cell are arranged so as to lie on a straight line, and said reagent sampling mechanism moves said nozzle along said straight line.

5. An automatic analyzer according to claim 1, further comprising a reagent sampling mechanism for moving said nozzle downwardly to insert said nozzle into said piercing tool to be locked therein with said lever, for moving said nozzle upwardly to remove said nozzle with said piercing tool locked thereto from said container, for moving said nozzle with said piercing tool locked thereto laterally, for inserting said nozzle with said piercing tool locked thereto into said container, and for moving said nozzle with said piercing tool locked thereto upwardly to move said lever to unlock said lever from said nozzle.

6. An automatic analyzer according to claim 1, wherein said piercing tool has a slidable guide tube thereon and said seal of said at least one reagent bottle has a recess therein to be engaged with said slidable guide tube for positioning said opposite end of said piercing tool accurately relative to said reagent bottle.

* * * * *